(12) United States Patent
Schorn

(10) Patent No.: US 6,910,906 B2
(45) Date of Patent: Jun. 28, 2005

(54) CONNECTOR ASSEMBLY

(75) Inventor: Greg Schorn, Milford, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 98 days.

(21) Appl. No.: 10/699,369

(22) Filed: Oct. 31, 2003

(65) Prior Publication Data

US 2005/0095891 A1 May 5, 2005

(51) Int. Cl.[7] .............................................. H01R 13/52
(52) U.S. Cl. ..................... 439/274; 439/909; 439/585; 439/462; 607/122
(58) Field of Search .................. 439/909, 274, 439/275, 589, 585, 462; 607/37, 116, 122, 123

(56) References Cited

U.S. PATENT DOCUMENTS

| | | | |
|---|---|---|---|
| 1,983,840 A | 12/1934 | Dohner | |
| 2,412,664 A | 12/1946 | Wolfram et al. | |
| 2,450,314 A | 9/1948 | Vandervoort | |
| 2,452,890 A | 11/1948 | Wolfram | |
| 2,547,889 A | 4/1951 | Richardson | |
| 4,025,093 A | 5/1977 | Leczycki | |
| 4,138,145 A | 2/1979 | Lawrence | |
| 4,613,158 A | 9/1986 | Ekman | |
| 4,950,255 A | * 8/1990 | Brown et al. | 604/250 |
| 6,062,902 A | * 5/2000 | Buckles et al. | 439/502 |
| 6,167,291 A | * 12/2000 | Barajas et al. | 600/374 |
| 6,183,305 B1 | * 2/2001 | Doan et al. | 439/668 |
| 6,199,432 B1 | * 3/2001 | Dunn | 73/756 |
| 6,671,554 B2 | * 12/2003 | Gibson et al. | 607/37 |

FOREIGN PATENT DOCUMENTS

| | | |
|---|---|---|
| EP | 0945662 A2 | 9/1999 |
| GB | 2047832 A | 12/1980 |
| GB | 2167147 A | 1/1987 |
| JP | 1238791 | 9/1989 |

* cited by examiner

*Primary Examiner*—Hien Vu
(74) *Attorney, Agent, or Firm*—Eugene T. Szczecina

(57) ABSTRACT

A connector connects a silicone or other radially expandable catheter to a catheter that does not expand radially. The catheter includes a hollow first connection part, a hollow second connecting part and a locking sleeve. The hollow second connecting part is threadably connected to the first connection part. The second part has a rib protruding from an external surface thereof. The rib has a recessed notch. A locking sleeve has a lip projecting radially inwardly therefrom at each end. The lip at the second end is fixedly received within the recessed notch. The lip at the first end is disposed about the external surface of the connection part. The locking sleeve is axially movable with respect to the first connection part. Axial movement of the locking sleeve in one direction is limited, thereby preventing disassembly of the first connecting part and the second connecting part.

24 Claims, 3 Drawing Sheets

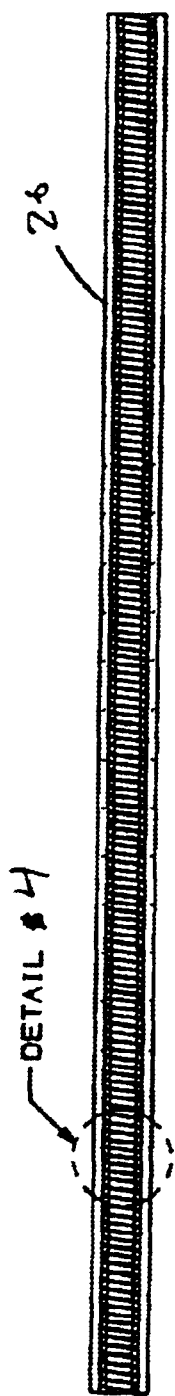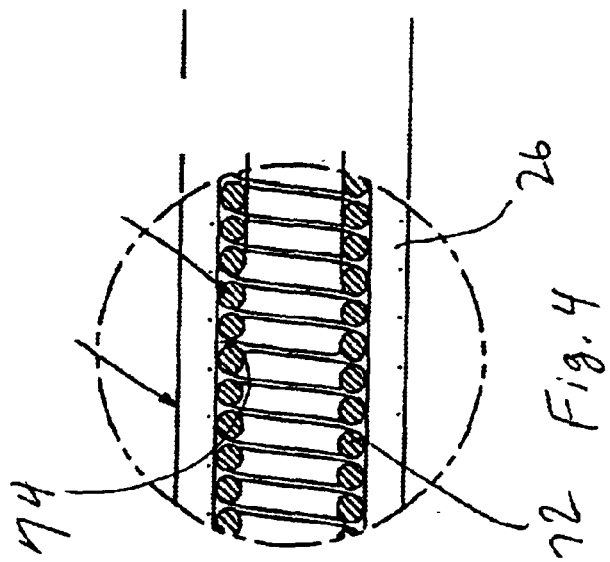

CONNECTOR ASSEMBLY

BACKGROUND OF THE INVENTION

1. Field of the Invention

The present invention relates to a connector assembly. More specifically, the present invention relates to a connector for fluidly connecting a silicone catheter to a catheter that does not expand radially.

2. Discussion of the Related Art

There are many connectors known to those skilled in the art for fluidly connecting one conduit to another. However, there has arisen a need in the medical field for a connector for connecting a silicone or other radially expandable catheter to a catheter that does not expand radially. These tyes of catheters are resistant to kinking and collapsing so that they remain open during use. However, because these types of catheters (hereinafter referred to as kink proof catheters) are essentially incapable of expanding radially, they cannot be attached to a connector by being placed about a conventional barb. Current connectors for kink proof catheters require the use of tools to tighten the connector to hold and seal the kink proof catheter. Additionally, once used, the internal compartment that seals and holds the kink proof catheter is permanently deformed. In addition, there is a need to provide a connector that cannot be disassembled. The present invention is directed to a connector that satisfies these needs.

SUMMARY OF THE INVENTION

The present invention provides a connector that connects a silicone or other radially expandable catheter to a catheter that does not expand radially. The catheter includes a hollow first connection part that has a first end and a second end. The first end has a barb protruding from an external surface thereof for connecting to the radially expandable catheter. The second end has an internal threaded surface, and an externally projecting annular rib. The internal surface extends from the second end to the first end with the internal threaded surface, a first bore, a first shoulder transitioning to a second reduced diameter bore, a second shoulder transitioning to a third further reduced diameter bore. The second shoulder has at least a portion thereof being beveled.

A hollow second connecting part is threadably connected to the first connection part. The second connecting part has a first end and a second end. The first end has an external threaded surface that mates with the internal threaded surface of the first connection part. The second part has a rib protruding from an external surface thereof. The rib has a recessed notch.

A locking sleeve has a first end and a second end. Each of the ends has a lip projecting radially inwardly therefrom. The lip at the second end is fixedly received within the recessed notch. The lip at the first end is disposed about the external surface of the first connection part on a side of the externally projecting annular rib remote from the second end of the first connection part. The locking sleeve is axially movable with respect to the first connection part. Axial movement in one direction is limited by abutment of the externally projecting annular rib of the first connection part and the inwardly projecting lip on the first end of the locking sleeve, thereby preventing disassembly of the first connecting part and the second connecting part.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 3 is cross-sectional view of the kink proof catheter, and FIG. 4 is an enlarged detail taken from detail circle 4 of FIG. 3.

DETAILED DESCRIPTION OF THE PRESENTLY PREFERRED EXEMPLARY EMBODIMENT

Figure 1:
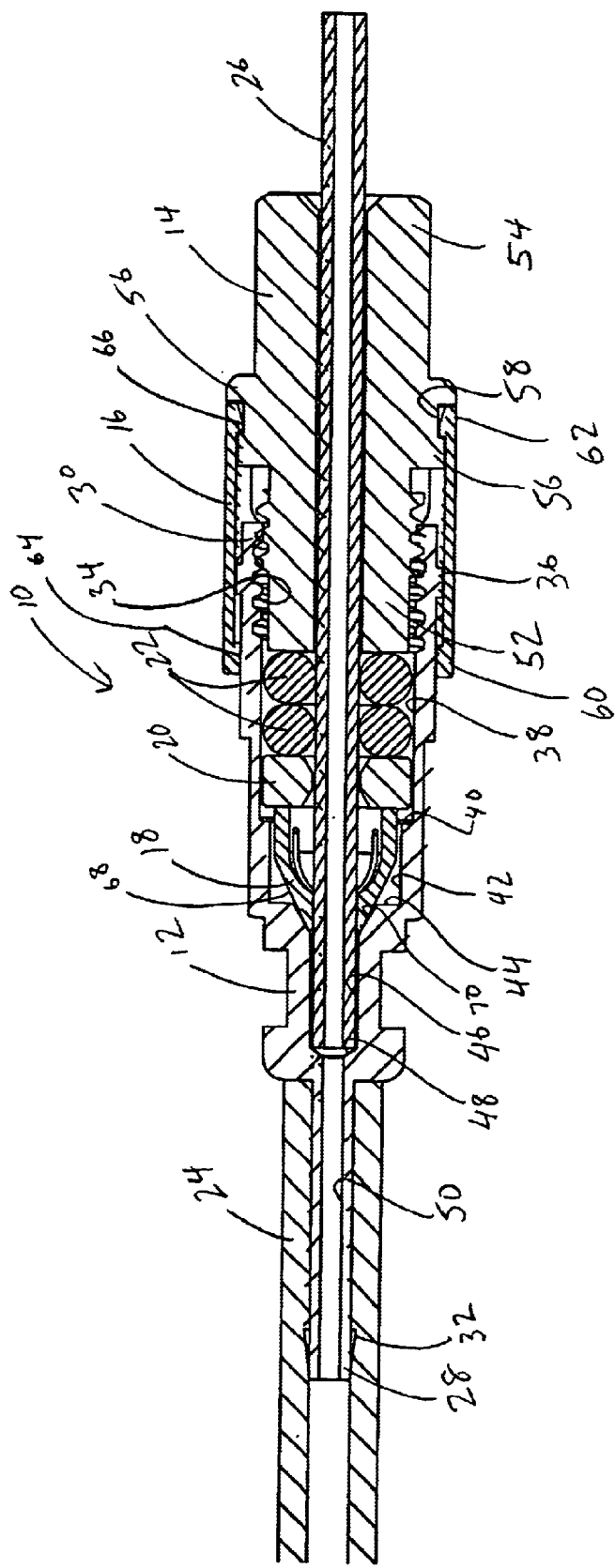
FIG. 1 is a cross-sectional view of the connector in accordance with the present invention.
Figure 2:
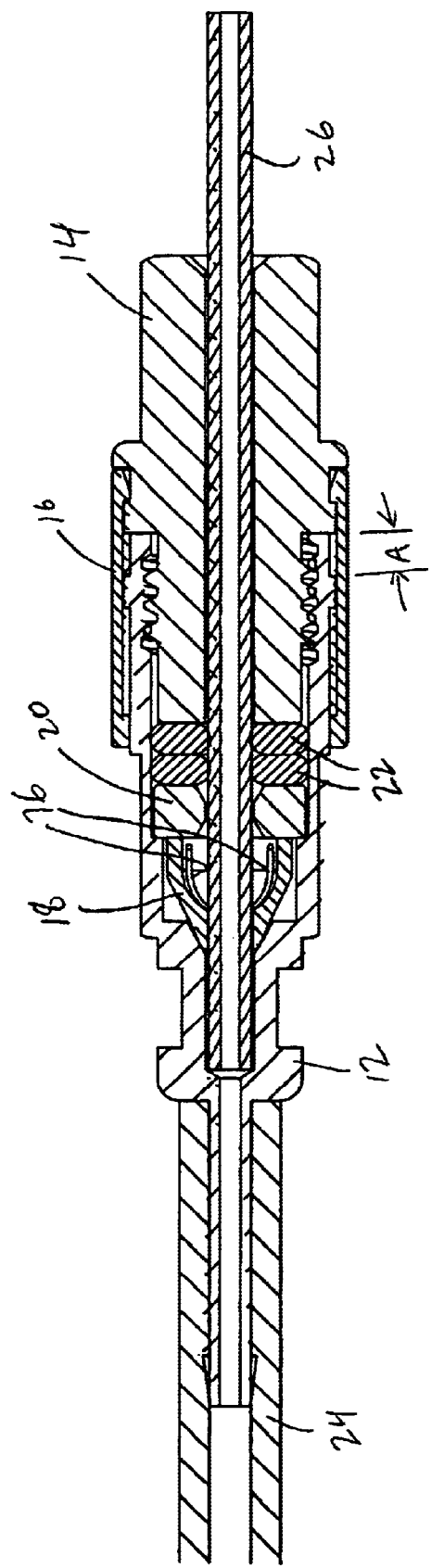
FIG. 2 is a cross-sectional view of the connector of FIG. 1, shown being fluidly connected to a kink proof catheter.

Referring now to FIGS. 1–3, a connector assembly 10 in accordance with the present invention is illustrated. The connector assembly includes a hollow first connection part 12, a second part 14, a locking sleeve 16, a collet 18, a spacer 20, and a pair of o-rings 22 for fluidly connecting a silicone catheter 24 to a kink proof catheter 26.

The first connecting part 12 has a first end 28 and a second end 30. The first end 28 has a barb 32 protruding from an external surface thereof for connecting to a silicone or other radially expandable catheter 24. The second end 30 has an internal threaded surface 34, and an externally projecting annular rib 36. The externally projecting annular rib 36 of the first connecting part 12 is disposed at a predetermined distance A from the second end 30.

The internal surface of the first connecting part 12 extends from the second end 30 to the first end 28 with the internal threaded surface 34, a first bore 38, a first shoulder 40 transitioning to a second reduced diameter bore 42, a second shoulder 44 transitioning to a third further reduced diameter bore 46, and a third shoulder 48 transitioning to a fourth still further reduced diameter bore 50. The second shoulder 44 has at least a portion thereof beveled along a radially inner portion thereof.

The hollow second connecting part 14 is threadably connected to the first connection part 12. The second connecting part 14 has a first end 52 and a second end 54. First end 52 has an external threaded surface 55 that mates with the internal threaded surface 34 of the first connection part 12. The second part 14 has a rib 56 protruding from an external surface thereof. Rib 56 has a recessed notch 58.

Locking sleeve 16 has a first end 60 and a second end 62. Each of the ends 60, 62 has a lip 64, 66, respectively, that projects radially inwardly therefrom. The lip 66 at the second end 62 is fixedly received within recessed notch 58. Lip 64 at the first end is disposed about the external surface of the first connection part 12 on a side of the externally projecting annular rib 36 remote from the second end 30 of the first connection part 12. The locking sleeve 16 is axially movable with respect to the first connection part 12. The axial movement in one direction (i.e., to the right as illustrated in the drawing figures) is limited by abutment of the externally projecting annular rib 36 of the first connection part 12 and the inwardly projecting lip 64 on the first end 60 of the locking sleeve 16, thereby preventing disassembly of said first connecting part 12 and the second connecting part 14 and all the parts contained therein.

A kink proof catheter 26 is disposed within at least a portion of the first connection part 12 and the second connection part 14. Kink proof catheter 26 has a soft outer surface with a wire-reinforced body. As shown in FIGS. 3 and 4, the kink proof catheter 26 includes a wire coil 72 connected to an internal surface 74 thereof. The wire is preferably made of titanium, and preferably has a diameter of about 0.005 inches. The coil-reinforced catheter body provides the firmness needed for insertion while providing resistance to kinking or collapsing, thus maintaining patency. The inner titanium coil wire 72 also provides radiopacity. This is helpful for confirming catheter position long after initial placement. One such catheter is available from Codman & Shurtleff, Inc. of Raynham, Mass., under the trade name FLEXTIP PLUS® catheter. However, due to the wire coil, the kink proof catheter is essentially inflexible to radial expansion. Thus, the kink proof catheter cannot be attached to a connector by being placed about a barb, such as barb 32, because the catheter 26 can not expand radially sufficiently to pass over barb 32.

A collet 18 is disposed about at least a portion of the kink proof catheter 26 and within the second bore 42 of the first connection part 12. The o-rings 22 are disposed about at least a portion of the kink proof catheter 26 and within the first bore 38 of the first connection part 12. A spacer 20 is disposed about at least a portion of the kink proof catheter 26 and within the first bore 38 of the first connection part 12. Spacer 20 is preferably disposed between collet 18 and the o-rings 22.

A silicone catheter 24 is disposed about the first end external surface of the first connection part 12. The silicone catheter is disposed about barb 32 to maintain the position of the catheter 24 with respect to the first connecting part 12. If desired a suture (not shown) may additionally be used to secure catheter 24 to the first connection part 12.

The collet 18 has an external beveled surface 68 that mates with a beveled portion 70 of second shoulder 44 of the first connection part 12. A radial inner portion of the second shoulder 44 included the beveled portion 70. Collet 18 includes a plurality of slots 76.

In use, the kink proof catheter 26 is placed within the second connection part 14 until its distal end abuts the third shoulder 48 of the first connection part 12. To hold and seal catheter 26 within the connector assembly 10, the user can then simply rotate second connecting part 14 with respect to first connecting part, thereby moving these parts from the position illustrated in FIG. 1 to the position illustrated in FIG. 2. During this movement the collet 18 is moved (to the left as illustrated in the drawing Figures) such that the collet's beveled surface 68 slides against beveled shoulder 70, thereby causing the distal end of the collet 18 to compress about catheter 26, thereby holding catheter in place. Collet 18 is compressed by forces that are below its yield strength. Thus, upon removal of the external force (e.g., unscrewing second connection part 14 from first connection part 12), the collet will return to its original position, and will no longer hold catheter 26. Therefore, the connector can be reused many times to hold and seal about a kink proof catheter. Simultaneously, this advancement of second part 14 into first part 12 causes o-rings 22 to. compress between the spacer 20 and the second part 14, thereby forming an effective seal about cather 26 and the internal surface of the second connecting part 12.

Thus, while there have been shown, described, and pointed out fundamental novel features of the invention as applied to a preferred embodiment thereof, it will be understood the various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitution of elements from one described embodiment to another are also fully intended and contemplated. It is also to be understood that the drawings are not necessarily drawn to scale, and maybe merely conceptual in nature. It is the intention, therefore, to be limited only as indicated by the scope of the claims appended hereto.

What is claimed is:

1. A connector assembly comprising:
   a hollow first connection part having a first end and a second end, said first end having a barb protruding from an external surface thereof for connecting to a silicon tube, said second end having an internal threaded surface, and an externally projecting annular rib, said internal surface extending from said second end to said first end with said internal threaded surface, a first bore, a first shoulder transitioning to a second reduced diameter bore, a second shoulder transitioning to a third further reduced diameter bore, said second shoulder having at least a portion thereof being beveled;
   a hollow second connecting part being threadably connected to said first connection part, said second connecting part having a first end and a second end, said first end having an external threaded surface that mates with the internal threaded surface of said first connection part, said second part having a rib protruding from an external surface thereof, said rib having a recessed notch;
   a locking sleeve having a first end and a second end, each of said ends having a lip projecting radially inwardly therefrom, said lip at said second end being fixedly received within said recessed notch, said lip at said first end being disposed about said external surface of said first connection part on a side of said externally projecting annular rib of said first connection part remote from said second end of said first connection part, said locking sleeve being axially movable with respect to said first connection part, said axial movement in one direction being limited by abutment of said externally projecting annular rib of said first connection part and said inwardly projecting lip on said first end of said locking sleeve, thereby preventing disassembly of said first connecting part and said second connecting part;
   a kink proof catheter being disposed within at least a portion of said first connection part and said second connection part, said kink proof catheter being essentially inflexible to radial expansion thereof;
   a collet being disposed about at least a portion of said kink proof catheter and within said second bore of said first connection part;
   at least one o-ring being disposed about at least a portion of said kink proof catheter and within said first bore of said first connection part;
   a spacer being disposed about at least a portion of said kink proof catheter and within said first bore of said first connection part; and
   a silicone catheter being disposed about said first end external surface of said first connection part.

2. The connector assembly according to claim 1, wherein said collet has an external beveled surface that mates with the beveled second shoulder of said first connection part.

3. The connector assembly according to claim 1, wherein said spacer is disposed between said collet and said at least one o-ring.

4. The connector assembly according to claim 1, wherein said externally projecting annular rib of said first connecting part is disposed at a predetermined distance from said second end.

5. The connector assembly according to claim 1, wherein said internal surface of said first connection part further includes a third shoulder transitioning to a fourth further reduced diameter bore.

6. The connector assembly according to claim 1, wherein a radial inner portion of said second shoulder of said first connection part includes said beveled portion.

7. The connector assembly according to claim 6, wherein said collet has an external beveled surface that mates with the beveled second shoulder portion of said first connection part.

8. The connector assembly according to claim 1, wherein said kink proof catheter includes a wire coil connected to an internal surface thereof.

9. The connector assembly according to claim 8, wherein said wire is made of titanium.

10. The connector assembly according to claim 9, wherein said wire has a diameter of about 0.005 inches.

11. The connector assembly according to claim 1, wherein said collet includes a plurality of slots.

12. The connector assembly according to claim 1, wherein said silicone catheter is disposed about said barb.

13. A connector comprising:
a hollow first connection part having a first end and a second end, said first end having a barb protruding from an external surface thereof for connecting to a silicon tube, said second end having an internal threaded surface, and an externally projecting annular rib, said internal surface extending from said second end to said first end with said internal threaded surface, a first bore, a first shoulder transitioning to a second reduced diameter bore, a second shoulder transitioning to a third further reduced diameter bore, said second shoulder having at least a portion thereof being beveled;
a hollow second connecting part being threadably connected to said first connection part, said second connecting part having a first end and a second end, said first end having an external threaded surface that mates with the internal threaded surface of said first connection part, said second part having a rib protruding from an external surface thereof, said rib having a recessed notch;
a locking sleeve having a first end and a second end, each of said ends having a lip projecting radially inwardly therefrom, said lip at said second end being fixedly received within said recessed notch, said lip at said first end being disposed about said external surface of said first connection part on a side of said externally projecting annular rib of said first connection part remote from said second end of said first connection part, said locking sleeve being axially movable with respect to said first connection part, said axial movement in one direction being limited by abutment of said externally projecting annular rib of said first connection part and said inwardly projecting lip on said first end of said locking sleeve, thereby preventing disassembly of said first connecting part and said second connecting part;
a collet being disposed within said second bore of said first connection part for selectively fixedly engaging with the outer surface of a kink proof catheter;
at least one o-ring being disposed within said first bore of said first connection part for selectively sealingly engaging with the outer surface of a kink proof catheter; and
a spacer being disposed within said first bore of said first connection part.

14. The connector according to claim 13, wherein said collet has an external beveled surface that mates with the beveled second shoulder of said first connection part.

15. The connector according to claim 13, wherein said spacer is disposed between said collet and said at least one o-ring.

16. The connector according to claim 13, wherein said externally projecting annular rib of said first connecting part is disposed at a predetermined distance from said second end.

17. The connector according to claim 13, wherein said internal surface of said first connection part further includes a third shoulder transitioning to a fourth further reduced diameter bore.

18. The connector according to claim 13, wherein a radial inner portion of said second shoulder of said first connection part includes said beveled portion.

19. The connector according to claim 18, wherein said collet has an external beveled surface that mates with the beveled second shoulder portion of said first connection part.

20. The connector according to claim 13, wherein said collet includes a plurality of slots.

21. A connector comprising:
a hollow first connection part having a first end and a second end, said first end having a barb protruding from an external surface thereof for connecting to a silicon tube, said second end having an internal threaded surface, and an externally projecting annular rib, said internal surface extending from said second end to said first end with said internal threaded surface, a first bore, a first shoulder transitioning to a second reduced diameter bore, a second shoulder transitioning to a third further reduced diameter bore, said second shoulder having at least a portion thereof being beveled;
a hollow second connecting part being threadably connected to said first connection part, said second connecting part having a first end and a second end, said first end having an external threaded surface that mates with the internal threaded surface of said first connection part, said second part having a rib protruding from an external surface thereof, said rib having a recessed notch; and
a locking sleeve having a first end and a second end, each of said ends having a lip projecting radially inwardly therefrom, said lip at said second end being fixedly received within said recessed notch, said lip at said first end being disposed about said external surface of said first connection part on a side of said externally projecting annular rib of said first connection part remote from said second end of said first connection part, said locking sleeve being axially movable with respect to said first connection part, said axial movement in one direction being limited by abutment of said externally projecting annular rib of said first connection part and said inwardly projecting lip on said first end of said locking sleeve, thereby preventing disassembly of said first connecting part and said second connecting part.

22. The connector according to claim 21, further comprising a collet being disposed within said second bore of said first connection part for selectively fixedly engaging with the outer surface of a kink proof catheter.

23. The connector according to claim 22, further comprising at least one o-ring being disposed within said first bore of said first connection part for selectively sealingly engaging with the outer surface of a kink proof catheter.

24. The connector according to claim 23, further comprising a spacer being disposed within said first bore of said first connection part between said collet and said at least one o-ring.

* * * * *